United States Patent
Komatsu et al.

Patent Number: 5,227,395
Date of Patent: Jul. 13, 1993

[54] ANTI-PLATELET AGGREGATING AGENT

[75] Inventors: Hirohiko Komatsu, Tokyo; Einosuke Sakurai, Saitama; Fumiko Hamaguchi, Tokyo; Tatsuo Nagasaka, Tokyo, all of Japan

[73] Assignee: Nisshin Flour Milling Co., Ltd., Tokyo, Japan

[21] Appl. No.: 854,904

[22] Filed: Mar. 20, 1992

[30] Foreign Application Priority Data

Mar. 25, 1991 [JP] Japan ................... 3-83048

[51] Int. Cl.$^5$ ............................ A61K 31/40
[52] U.S. Cl. ................... 514/408; 514/418; 514/422; 514/423; 514/427; 514/822
[58] Field of Search ............... 514/408, 418, 422, 423, 514/427, 822; 548/538, 539

[56] References Cited

U.S. PATENT DOCUMENTS

| | | | |
|---|---|---|---|
| 2,829,146 | 4/1958 | Beaver et al. | 548/538 |
| 4,118,396 | 10/1978 | Pifferi et al. | 548/538 |
| 4,369,139 | 1/1983 | Kybarz et al. | 548/539 |

FOREIGN PATENT DOCUMENTS

| | | |
|---|---|---|
| 0304330 | 2/1989 | European Pat. Off. . |
| 0443474 | 8/1991 | European Pat. Off. . |
| 1583871 | 2/1981 | United Kingdom |

OTHER PUBLICATIONS

Nature, No. 4832, Jun. 9, 1962, pp. 927–929, G. V. R. Born, "Aggregation of Blood Platelets by Adenosine Diphosphate and Its Reversal".
The Lancet, vol. 2, No. 8145, pages 752–753, Oct. 6, 1979, R.L. Bick, "In-Vivo Platelet Inhibition of Piracetam."

Primary Examiner—Frederick E. Waddell
Assistant Examiner—K. Weddington
Attorney, Agent, or Firm—Oblon, Spivak, McClelland, Maier & Neustadt

[57] ABSTRACT

The use of 1-phenoxycarbonyl-2-pyrrolidinone derivatives as an anti-platelet aggregating agent. The derivatives are of the formula

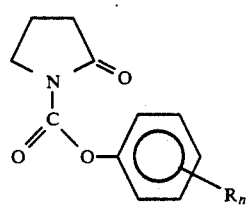

wherein R is a $C_1$–$C_6$ alkyl group, a $C_1$–$C_6$ alkoxy group, a nitro group or a halogen atom and n is 0, 1 or 2.

3 Claims, No Drawings

ANTI-PLATELET AGGREGATING AGENT

FIELD OF THE INVENTION

This invention is concerned with the use of 1-phenoxycarbonyl-2-pyrrolidinone derivatives having an anti-platelet aggregating activity for the prevention of vascular diseases. More particularly, the invention relates to anti-platelet aggregating agents.

BACKGROUND OF THE INVENTION

European Patent 0 304 330 A1 discloses that 1-phenoxycarbonyl-2-pyrrolidinone is an intermediate for the preparation of carbamoylpyrrolidone derivatives which are useful as drugs for senile dementia, or as psychotropic and/or antiamnesia agents.

European Patent 0 443 474 A2 also discloses the use of 1-phenoxycarbonyl-2-pyrrolidinone and its substituted phenyl derivatives as nootropic agents.

There is no reference about other pharmaceutical uses of 1-phenoxycarbonyl-2-pyrrolidinone derivatives.

DISCLOSURE OF THE INVENTION

In view of such situations, we have investigated further medical use of 1-phenoxycarbonyl-2-pyrrolidinone derivatives as disclosed in EPA 0 443 474 A2 and found that they possess a potent anti-platelet aggregating activity and are useful for the prevention of vascular diseases such as thrombosis, cardiac infarction, cerebral infarction and arterial sclerosis and preventing the development or recurrence of such diseases.

Thus the present invention provides a method for preventing a platelet aggregation in a mammal which comprises administering to the mammal an anti-platelet aggregation effective amount of a compound of the formula

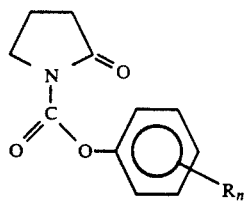

wherein R is a $C_1$–$C_6$ alkyl group, a $C_1$–$C_6$ alkoxy group, a nitro group or a halogen atom and n is 0, 1 or 2.

The invention also provides an anti-platelet aggregating agent comprising said compound as an active agent.

In the above formula, the $C_1$–$C_6$ alkyl group includes preferably straight or branched alkyl groups of 1–4 carbon atoms, e.g., methyl, ethyl, isopropyl, n-propyl, isobutyl, tert.-butyl and n-butyl. The $C_1$–$C_6$ alkoxy group includes preferably straight or branched alkyl groups of 1–4 carbon atoms, e.g., methoxy, ethoxy, isopropoxy, n-propoxy, isobutoxy, tert.-butoxy, and n-butoxy. The halogen atom includes fluorine, chorine and bromine.

The compounds of the invention can be prepared by reacting phenol or substituted phenol with phosgen to form corresponding cloroformylated phenol or substituted phenol followed by reacting with 2-pyrrolidinone or a reactive derivative of 2-pyrrolidinone, for example, 1-trimethylsilyl-2-pyrrolidinone.

Representative compounds of the present invention are shown in Table 1.

TABLE 1

| Compound No. | Name | Formula | M.P. |
|---|---|---|---|
| 1 | 1-(Phenoxycarbonyl)-2-pyrrolidinone | | 123–124° C. |
| 2 | 1-(2'-Methoxyphenoxycarbonyl)-2-pyrrolidinone | | 104–105° C. |
| 3 | 1-(3'-Methoxyphenoxycarbonyl)-2-pyrrolidinone | | 45–47° C. |
| 4 | 1-(4'-Methoxyphenoxycarbonyl)-2-pyrrolidinone | | 133–134° C. |

TABLE 1-continued

| Compound No. | Name | M.P. |
|---|---|---|
| 5 | 1-(2'-Methylphenoxycarbonyl)-2-pyrrolidinone | 85–87° C. |
| 6 | 1-(3'-Methylphenoxycarbonyl)-2-pyrrolidinone | 58–59° C. |
| 7 | 1-(4'-Methylphenoxycarbonyl)-2-pyrrolidinone | 101–102° C. |
| 8 | 1-(4'-Fluorophenoxycarbonyl)-2-pyrrolidinone | 89–90° C. |
| 9 | 1-(2'-Chlorophenoxycarbonyl)-2-pyrrolidinone | 92–93° C. |
| 10 | 1-(3'-Chlorophenoxycarbonyl)-2-pyrrolidinone | 88–89° C. |
| 11 | 1-(4'-Chlorophenoxycarbonyl)-2-pyrrolidinone | 99–100° C. |
| 12 | 1-(2'-Bromophenoxycarbonyl)-2-pyrrolidinone | 103–104° C. |

TABLE 1-continued

| Compound No. | Name | Formula | M.P. |
|---|---|---|---|
| 13 | 1-(3'-Bromophenoxycarbonyl)-2-pyrrolidinone | | 95–96° C. |
| 14 | 1-(4'-Bromophenoxycarbonyl)-2-pyrrolidinone | | 107–108° C. |
| 15 | 1-(2'-Nitrophenoxycarbonyl)-2-pyrrolidinone | | 135–136° C. |
| 16 | 1-(3'-Nitrophenoxycarbonyl)-2-pyrrolidinone | | 130–131° C. |
| 17 | 1-(4'-Nitrophenoxycarbonyl)-2-pyrrolidinone | | 122–123° C. |
| 18 | 1-(2',6'-Dimethoxyphenoxycarbonyl)-2-pyrrolidinone | | 163–165° C. |
| 19 | 1-(3',5'-Dimethoxyphenoxycarbonyl)-2-pyrrolidinone | | 80–81° C. |

The anti-platelet aggregating activity of the compounds of the present invention was determined by Born's turbidimetric method (G.V.R. Born, Nature, No. 4832, Jun. 9, 1962, 927–929) using an aggregometer (NKK Hema Tracer 1, PAT-4M, NKK Inc. Japan).

1. Materials and Method 1.1. Preparation of platelet-rich plasma (PRP)

PRP was prepared from male Japanese white rabbits weighing 2.3–4.1 kg. Blood was drawn into syringes containing 3.8% sodium citrate (1/10 volume) and centrifuged at 1000 r.p.m. for 10 min. at room temperature.

Platelet poor plasma (PPP) was obtained from the supernatant fraction of the residual blood by centrifugation at 3000 r.p.m. for 10 min. The aggregation (%) was calculated against the turbidity of PPP, which was designated as 100%. 1.2. In vitro anti-platelet test A 200 μl volume of PRP was placed in the cuvette of the aggregometer and incubated at 37° C. To the cuvette was added 25 μl of 10% methanol solution in physiological saline as a solvent or 25 μl of test drug solution dissolved in the solvent in a predetermined concentration (μg/ml) indicated in Table 2, which was stirred and incubated. 5 min. after, platelet aggregation was induced by the addition of 25 μl of $10^{-2}$M arachidonic acid. Changes in the percentage of aggregation was recorded on a multirecorder (T626-DS, NKK Inc., Japan). 1-(4'-Methoxybenzoyl)-2-pyrrolidinone (aniracetam) was used as a control compound.

2. Result

The percentage inhibition (I) of platelet aggregation by a test drug was calculated from the following equation:

$$I(\%) = (1 - A/B) = 100$$

in which A is the percentage maximum aggregation for addition of the drug and B is the percentage maximum aggregation for no addition of the drug. The result is shown in Table 2.

TABLE 2

| Test drug | Percentage inhibition of platelet aggregation (%) | | | |
|---|---|---|---|---|
| | 10 | 25 | 50 | 100 (μg/ml) |
| Aniracetam | | | 0.4 | 4.1 |
| Compound No. 2 | 40.9 | 69.8 | 81.6 | 96.2 |
| Compound No. 3 | | | 8.5 | 28.6 |
| Compound No. 4 | 51.1 | 72.5 | 95.5 | 98.2 |
| Compound No. 5 | 5.0 | 35.8 | 50.6 | 92.3 |
| Compound No. 6 | | | 4.7 | 39.7 |
| Compound No. 7 | 5.8 | 31.0 | 70.6 | 97.7 |
| Compound No. 18 | 26.0 | 64.8 | 90.9 | 96.4 |

The Compound No. in the table corresponds to that shown in Table 1.

The compound of the present invention can be formulated in various dosage forms. The pharmaceutical preparations can be administered orally in the form of tablets, sugar-coated tablets, hard capsules, soft capsules or liquids such as solutions, emulsions or suspensions. Alternatively, the preparations may be administered ractally in the form of suppositories or parenterally in the form of injections.

These pharmaceutical preparations can be produced by known processes using additives well known in the art such as excipients, binders, diluents, stabilizers, preservatives, solubilizers, wetting agents, emulsifiers, lubricants, sweetners, colorants, flavoring agents, buffers and antioxidants. The compounds of the invention can be used for the prevention of vascular diseases such as thrombosis, cardiac infarction, cerebral infarction and arterial sclerosis and for preventing the development or recurrence of such diseases. Dosage of the present compounds is variable in a wide range, generally a daily dose of about 5 to 2500 mg/kg.

The following examples illustrate the pharmaceutical preparations of the compounds according to the present invention.

EXAMPLE 1 - Tablets (one tablet)

| 1-(4'-Methoxyphenoxycarbonyl)-2- | 10 mg |
|---|---|

| -continued | |
|---|---|
| pyrrolidinone | |
| Lactose | 67 mg |
| Crystalline cellulose | 15 mg |
| Corn starch | 7 mg |
| Magnesium stearate | 1 mg |
| | 100 mg |

The components were uniformly blended to prepare powders for direct compression. The powders were formulated by a rotary tableting machine into tablets each 6 mm in diameter and weighing 100 mg.

EXAMPLE 2 - Granules (one divided form)

| 1-(4'-Methoxyphenoxycarbonyl)-2- | 10 mg |
|---|---|
| pyrrolidinone | |
| Lactose | 90 mg |
| Corn starch | 50 mg |
| Crystalline cellulose | 50 mg |
| Hydroxypropylcellulose | 10 mg |
| Ethanol. | 90 mg |

The above components except for hydroxypropylcellulose and ethanol were uniformly blended and then a solution of hydroxypropylcellulose and ethanol was added. The mixture was kneaded and granulated by extrusion granulation. The granules were dried in a drier at 50° C. and screened to particle sizes of 297 μm–1460 μm. The granular formulation was divided into 200 mg per division.

EXAMPLE 3 - Syrup

| 1-(4'-Methoxyphenoxycarbonyl)-2- | 1.000 g |
|---|---|
| pyrrolidinone | |
| Sucrose | 30.000 g |
| D-Sorbitol 70 w/v % | 25.000 g |
| Ethyl paraoxybenzoate | 0.030 g |
| Propyl paraoxybenzoate | 0.015 g |
| Flavors | 0.200 g |
| Glycerin | 0.150 g |
| 96% Ethanol | 0.500 g |
| Distilled water | q.s. |
| Total | 100 ml |

Sucrose, D-sorbitol, methyl paraoxybenzoate, propyl paraoxybenzoate and the above pyrrolidinone were dissolved in 60 g of warm water. To the solution, after cooling, were added glycerin and the flavors dissolved in the ethanol. To the mixture was then added water to make up 100 ml.

EXAMPLE 4 - Injections

| 1-(4'-Methoxyphenoxycarbonyl)-2- | 2 mg |
|---|---|
| pyrrolidinone | |
| CMC | 2 mg |
| Distilled water | 1 mg |

CMC and the above pyrrolidinone were suspended in distilled water to prepare an injection.

EXAMPLE 5 - Suppositories

| 1-(4'-Methoxyphenoxycarbonyl)-2- | 2 g |
|---|---|
| pyrrolidinone | |
| Polyethylene glycol 4000 | 20 g |
| Glycerin | 78 g |

| -continued |
| --- |
| Total 100 g |

The above pyrrolidinone was dissolved in glycerin. To the solution was added polyethylene glycol 4000, and the mixture was warmed to a solution. The solution was poured into a suppository mold and solidified by cooling to prepare suppositories weighing 1.5 g per piece.

What is claimed is:

1. A method for preventing platelet aggregation in a mammal which comprises administering to the mammal an anti-platelet aggregation effective amount of a compound of the formula

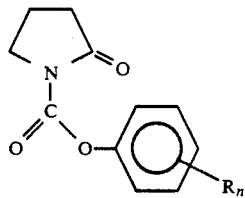

wherein R is a $C_1$–$C_6$ alkyl group, a $C_1$–$C_6$ alkoxy group, a nitro group or a halogen atom and n is 0, 1 or 2.

2. A method of claim 1 wherein R is a $C_1$–$C_4$ alkyl group.

3. A method of claim 1 wherein R is a $C_1$–$C_4$ alkoxy group.

* * * * *